(12) United States Patent
Strohschein et al.

(10) Patent No.: US 11,885,786 B1
(45) Date of Patent: Jan. 30, 2024

(54) INSECT OLFACTOMETER

(71) Applicant: Sigma Scientific LLC, Micanopy, FL (US)

(72) Inventors: Rudolph Strohschein, Micanopy, FL (US); James B. Estaver, Gainesville, FL (US); William Toreki, Gainesville, FL (US); David Mays, Gainesville, FL (US); Neil H. Weinstein, Gainesville, FL (US)

(73) Assignee: Sigma Scientific LLC, Micanopy, FL (US)

( * ) Notice: Subject to any disclaimer, the term of this patent is extended or adjusted under 35 U.S.C. 154(b) by 0 days.

(21) Appl. No.: 17/589,850

(22) Filed: Jan. 31, 2022

Related U.S. Application Data

(60) Provisional application No. 63/143,047, filed on Jan. 29, 2021.

(51) Int. Cl.
 *G01N 33/00* (2006.01)
(52) U.S. Cl.
 CPC ..... *G01N 33/0027* (2013.01); *G01N 33/0001* (2013.01)
(58) Field of Classification Search
 CPC .............. G01N 33/0027; G01N 33/0001
 USPC ........................................ 73/23.34
 See application file for complete search history.

(56) References Cited

U.S. PATENT DOCUMENTS

| 5,541,851 A * | 7/1996 | Sato | G01N 33/0031 |
| | | | 700/266 |
| 9,642,570 B2 * | 5/2017 | Acree | B05B 12/1472 |
| 2012/0103060 A1 * | 5/2012 | Brasfield | G01N 33/0001 |
| | | | 73/23.34 |
| 2020/0333305 A1 * | 10/2020 | Folli | G01N 33/0001 |

FOREIGN PATENT DOCUMENTS

| CN | 101213958 | 7/2008 |
| CN | 103995101 | 8/2014 |
| GB | 2448129 | 10/2008 |
| WO | WO/2008/117094 | 8/2008 |

OTHER PUBLICATIONS

Martin Luquet et al. Early Olfactory Environment Influences Antennal Sensitivity and Choice of the Host-Plant Complex in a Parasitoid Wasp, Insects 2019, 10, 127 (Year: 2019).*
Sigma Scientific LLC, Setting the standard for Insect Stimulus-Response Systems. Products & Services Guide (Year: 2019).*
Seung-Hye Jung et al., Odor-identity dependent motor programs underlie behavioral responses to odors, eLife, 2015; 4: e11092. (Year: 2015).*

(Continued)

*Primary Examiner* — Marrit Eyassu
(74) *Attorney, Agent, or Firm* — Elman Technology Law, P.C.; Gerry J. Elman; M. P. Moon

(57) ABSTRACT

An insect olfactometer is described. The olfactometer can be used to study the behavior and response of insects and other living organisms to odorants and airborne chemicals. The olfactometer provides one or more discrete odor zones that do not intersect with each other and are separated by a neutral background control odor zone.

17 Claims, 10 Drawing Sheets

(56) References Cited

OTHER PUBLICATIONS

McIndoo, N.E. An insect olfactometer, Journal of Economic Entomology, 19, pp. 545-571, (1926).
Luquet, Martin, et al. Early Olfactory Environment Influences Antennal Sensitivity and Choice of the Host-Plant etc. Insects, 10(5), p. 127, (2019).
Liu, B., et al. Development of 8-armed airflow olfactometers for measuring olfactory etc. Anz. Schadlingskde., Pflanzenschutz, Umweltschutz, 67, pp. 30-34 (1994).
Pettersson, J. An aphid sex attractant. I. Biological studies, Entomologia Scandinavica, 1, pp. 63-73, (1970).
Said, Imen, et al. Adaptation of a four-arm olfactometer for behavioural bioassays of large beetles. Chemoecology, 16 (1), pp. 9-16, Jan. 2006.
Leather, Simon. Entomological classics—The insect olfactometer, Don't Forget the Roundabouts, Jul. 28, 2020, https://simonleather.wordpress.com/.
Ren, L.I. et al. EAG response and behavioral orientation of Dastarcus helophoroides . . . to synthetic host-associated volatiles. PLoS ONE, 12 (12), (2017).
Masciocchi, M., et al. Drone aggregation behavior in the social wasp . . . Effect of kinship and density, Sci. Rep., 10, 7143 (2020).
VET Louise E. M., et al. An airflow olfactometer for measuring etc, Physiological Entomology: How Insects Work—Linking Genotype to Phenotype, 8 (1), p. 97-106 (Mar. 1983).

\* cited by examiner

INSECT OLFACTOMETER

TECHNICAL FIELD

The present invention relates to an apparatus and method for measuring and detecting an insect's ability to distinguish and be affected by various odors present in an atmospheric or vapor stream.

BACKGROUND

Olfactometry is the testing and measurement of the sense of smell, and the sensitivity thereof. Olfactometry also involves the study of how odors, scents, or airborne chemicals elicit a response by an organism.

An olfactometer is an instrument used to detect and measure odor concentration, or to control the intensity of odors presented to test subjects. An olfactometer is a device that can precisely detect and measure odor concentrations at various points or can deliver odors of controlled intensity to test subjects. Alternatively, an olfactometer can be a device used for producing aromas in a precise and controlled manner. Olfactometers can also be used to gauge the odor detection threshold for various substances, or to determine odor preferences. Olfactometers are commonly used in conjunction with human subjects in laboratory settings, most often in market research, to quantify and qualify human olfaction. To measure intensity, conventional olfactometers generally introduce an odorous gas as a baseline against which other odors are compared, without a clear odor boundary demarcation.

From an evolutionary point of view, olfaction (the sense of smell) is one of the oldest senses. It is used for seeking food, recognizing danger, reproduction, and communication. Olfaction is a protective sense that allows the detection of potential predators, toxins, illnesses, or infections by taking into account the odor palatability. Unpleasant odors may trigger a variety of emotional and undesirable reactions in human beings, varying from annoyance to adverse health effects.

Odorants are actually mixtures of volatile chemical molecules dispersed in air, which are able to stimulate a neurological response, either consciously or unconsciously. An odorant is a substance which incites the olfactory system so that an odor is perceived. The flavor or scent of a particular odor is given by the interaction of different volatile chemical species, including sulfur compounds (e.g., sulfides, mercaptans), nitrogen compounds (e.g., ammonia, amines), and volatile organic compounds (e.g., esters, acids, aldehydes, ketones, alcohols).

In vertebrate animals, odor (smell, scent, fragrance) is generally associated with the sense of smell (located in the nose or nasal cavity). These same chemical signals can also be perceived by other senses, such as taste. Taste is not necessarily confined to the tongue and mouth. For instance, it is speculated that some fish can perceive odors (taste or smell) directly through their skin. Lower forms of life, including arthropods (insects, arachnids, etc.) do not even have "noses" in the sense that vertebrates do; however, they can still sense "odors" (airborne chemical signals) using other body parts and structures—the "antennae" of insects, lobsters, and snails, for example. (Even plants and bacteria are capable of sensing "odors" even though the mechanisms are much different than true nasal odor perception used by vertebrates.

For the purposes of current invention, an "odorant" is defined as molecules of one or more chemicals capable of being detected, sensed, smelled, tasted, or perceived by a living organism. Such substances may exist as a gas or vapor, or may be airborne liquids or solutions (aerosols, mists), or airborne solids (such as smoke or dust cloud). Odor molecules may also be carried in a liquid (such as blood in water). The "odor" is distinct from the "zero", "background", or "neutral" medium (such as air) carrying the detectable molecules. In some cases, the medium may be made to intentionally contain other specific background odors.

The bulk of the scientific, patent, and commercial literature concerning olfactometry and olfactometers is concerned with testing human odor perception and preferences. Entomologists and other biologists also use olfactometry to understand the behavior of insects and similar organisms which use odors to search for nutrition, find mates, and avoid danger. Understanding which odors attract and repel insects allows scientists to control pests and to protect people, crops, and animals. This understanding has resulted in billions of dollars in cost savings to the worldwide economy.

The following patent and literature references describe various olfactometers that have been designed and used for olfaction studies by entomologists.

UK Patent Application 0705765 (GB2448129) of William Anthony Jonfia-Essien filed Mar. 24, 2007.

International Patent Application WO/2008/117094 of William Anthony Jonfia-Essien filed Mar. 25, 2008

Chinese Patent Application CN101213958 (200810056093.4) of China Agricultural University filed Jan. 11, 2008.

Chinese Patent Application CN103995101 (201410257676.9) of Beijing University of Agriculture filed Jun. 29, 2014.

McIndoo, N. E. *An insect olfactometer.* Journal of Economic Entomology, 19, p545-571, (1926).

Luquet, Martin, Olympe Tritto, Anne-Marie Cortesero, Bruno Jaloux, and Sylvia Anton, *Early Olfactory Environment Influences Antennal Sensitivity and Choice of the Host-Plant Complex in a Parasitoid Wasp,* Insects 10(5), p127, (2019), [https://doi.org/10.3390/insects10050127].

Liu, B., Şengonca, Ç., *Development of 8-armed airflow olfactometers for measuring olfactory responses of insect predators.* Anz. Schadlingskde., Pflanzenschutz, Umweltschutz 67, p30-34 (1994), [https://doi.org/10.1007/BF01907347].

Pettersson, J, *An aphid sex attractant I. Biological studies,* Entomologia Scandinavica 1, p63-73, (1970).

Said, Imen, Rosa Aldana de la Torre, Jean-Paul Morin, and Didier Rochat, *Adaptation of a four-arm olfactometer for behavioural bioassays of large beetles,* Chemoecology 16(1), p9-16, January (2006).

Leather, Simon *Entomological classics—The insect olfactometer, Don't Forget the Roundabouts* Jul. 28, (2020), https://simonleather.wordpress.com/.

Ren Ll, Balakrishnan K, Luo Y q, Schütz S, *EAG response and behavioral orientation of Dastarcus helophoroides (Fairmaire) (Coleoptera: Bothrideridae) to synthetic host-associated volatiles.* PLoS ONE 12(12), (2017), https://doi.org/10.1371/journal.pone.0190067.

Masciocchi, M., Angeletti, B., Corley, J. C. et al. *Drone aggregation behavior in the social wasp Vespula germanica (Hymenoptera: Vespidae):Effect of kinship and density.* Sci Rep 10, 7143 (2020). https://doi.org/10.1038/s41598-020-64232-9

Vet, Louise E. M., J. C. Van Lenteren, M. Heymans, E. Meelis. *An airflow olfactometer for measuring olfactory responses of hymenopterous parasitoids and other small*

*insects*. Physiological Entomology: How Insects Wrk—Linking Genotype to Phenotype Vol. 8, Issue 1, pages 97-106 March (1983). https://doi.org/10.1111/j.1365-3032.1983.tb00338.x In the following text, the foregoing literature references are cited by placing the last name of the primary author within parentheses, for example: (McIndoo).

Olfactometer experiments, in which arthropods are given the choice between two or more odor sources to test behavioral preferences, are commonly used in chemical ecology research. Results of such experiments often lead to conclusions on behavior in an ecologically relevant setting. In 1926, Norman McIndoo, a United States Dept. of Agriculture entomologist, invented the Y-tube olfactometer which revolutionized the study of insect behavior (McIndoo). The simplest olfactometer design to study insect behavior consists of a tube with a bifurcation (with "T" or "Y" wishbone shape) where an insect enters from the stem and moves to the "Y" junction where it decides between two choices, usually clean air versus air carrying an odor. This device is also called a "dual-choice" olfactometer. There is a tendency for turbulence to occur at the junction of the Y and T-tubes, which causes mixing of the test odors so that there is not a clearly delineated odor field into which the insects can enter, leave, and re-enter if they choose. The mixing of test odor also causes a dilution, creating a gradient between the junction and inlet arm.

In more recent years, olfactometers with additional arms have been used and commercialized for insect research. For instance, 3-, 4- and even 8-way olfactometers have been described (Luquet, Liu). Originally, the four-armed olfactometer was designed by Pettersson (Pettersson). The work of Pettersson ushered-in many studies using olfactometry for different investigations. For example, Vet describes a modified four-arm olfactometer (Vet), as do (Said) and (Masciocchi). All of these "traditional" or "conventional" olfactometers use a design where the individual odor streams enter from the periphery of the olfactometer, and are sucked, or pushed, towards a central point. The test subject(s) is generally placed at the center to begin its path toward making a choice between the individual odor streams.

Unfortunately, previous olfactometers designed to study insects and other lower organisms suffer from a major flaw. Namely, the individual odor streams intermix at or near the juncture of the separate tubes or arms introducing the odors (generally at the central point). This makes it virtually impossible to accurately evaluate the choice made by the insect, since it is not able to independently sample each odor stream compared to a non-odor background (or neutral) area. The odor signals may interact with each other to produce altered sensations. For instance, the combination of an appetizing odor with a disgusting odor could prevent one from being able to distinguish or detect any appetizing contribution to the overall odor of the mix.

For example, imagine a "wine tasting" where four different wines are mixed together in a single glass, then the subject is asked to decide which one they like best. It is better to present each odor individually, with exposure to the background neutral odor in-between. This is like the cleansing of one's palate between tastes of wine.

The various odor streams can also bind, neutralize, or chemically react with each other. The subject's detection sites (taste buds) can be blinded or saturated with one odor, preventing perception of other odorants. It would be much better if the olfactometer design allowed for the test subject to move about within a neutral, or defined, background odor zone, so that it can encounter and sample each discrete odor zone separately. In many cases, the compounds being studied are very similar in chemical structure and in scent, so keeping them separate is very important for determining sensory differences between similar compounds (such as cis- or trans-isomers of a molecule, or lengths of alkyl groups such as $C_{12}$ vs. $C_{14}$ fatty acid esters).

The Y-tube design also results in diluting the initial concentration of each odor when the two input odor streams merge. Also, when the insect is crawling it often stays on a straight path rather than random one, which prevents detection of the complete odor stream at the junction.

Entomologists generally employ a design whereby an odor compound of interest (or mixture of compounds) is volatilized into a carrier gas, usually air, which is then transferred as a vapor stream to a test chamber, or enclosed area, containing the test subject(s) (such as insects). The response from the subject can be an attraction or repulsion (or neutral) to the test sample, but might be of a more complex nature. Behavior change, such as flight or walking pattern alteration, of the test subject may occur and, at higher concentrations the test compound may be not only an attractant or a repellent but might also have toxic or pharmacological effects. It is necessary to accurately monitor various concentrations of the test compound during the bioassay—generally beginning at a very low level and gradually increasing the test sample concentration until a definitive response or variance in behavior occurs. This establishes a "threshold response value," and further increases in concentration may reveal other response changes.

SUMMARY OF THE INVENTION

The improved insect olfactometer of the current invention is a scientific research instrument and system to facilitate the study of how insects and other lower species respond to the effect of odors and scents. The insect olfactometer of the current invention provides one or more "discrete odor zones" within an enclosure defining an enclosed space. The enclosure comprises a means for inserting and releasing test subjects into the olfactometer. The olfactometer also provides one or more "defined background odor zones". The defined background odor zone allows a test subject to adjust to a constant neutral environment with baseline odor until separately approaching, or sampling, each discrete odor zone. The discrete odor zones within the enclosed space are spatially distinct from each other separated by defined background odor zone(s), and the test subject can only access, approach, or enter into, a discrete odor zone from within a defined background odor zone.

The present olfactometer is an improvement over previous insect olfactometers, in that it does not employ the conventional multi-choice olfactometer design of sucking multiple odor streams into a central exhaust point where the individual odors combine. The design of the present olfactometer recognizes the importance of separate controlled odor zones. These odor zones are established by employing a removal port for each introduction port thereby restricting (controlling) the sample to the area between these two ports. By controlling, during the design stage, the distance between the inlet and outlet, a well-defined area is established without bleeding sample into the background and causing contamination.

Definitions

For the purposes of the current description, an "odorant" is defined as molecules of one or more substances capable of being detected, sensed, smelled, tasted, or perceived by a living organism. The molecules may exist as a gas or vapor, or may be airborne liquids or solutions (aerosols, mists), or airborne solids (such as smoke or dust cloud). Odor molecules may also be carried in a liquid (such as blood in water).

A "Vapor stream" or "Fluid odorant stream" is a flow of fluid containing odorant, typically gaseous but optionally aerosols or fine particulates as described above.

"Enclosed space" refers to the interior of an olfactometer that is bounded by an enclosure. The enclosure separates the enclosed space from the outer environment. The enclosed space is sealed from the outside environment, except for specific inlet and outlet ports, such as for creation and maintenance of the discrete odor zones, defined background odor zone, the means for inserting and releasing a test subject into the enclosed space, and other designed parts (such as sampling ports).

"Test subject" refers to any living organism placed inside the enclosed area of the olfactometer.

"Defined background odor zone" is the part of the enclosed space of the olfactometer that is not occupied by a discrete odor zone. It can have a neutral odor or be devoid of odor, or it can have a pre-determined composition—i.e., the background environment. It allows a test subject to adjust to a constant neutral environment with no odor, or with a specific baseline (background) odor.

"Discrete odor zone" is a volume of space occupied by a test odorant being investigated. The concentration of odorant molecules within the discrete odor zone is controlled by the experimenter. Generally, the discrete odor zones are partially or fully surrounded by a defined background odor zone. The boundaries of the discrete odor zones may also be partially determined by the walls or perimeter of the enclosed space. A discrete odor zone should not overlap or intersect with another discrete odor zone. The discrete odor zone may sometimes have a composition that is identical to the defined background zone (for "control" experiments). The discrete odor zone may alternatively omit a component of the defined background odor zone (a "reverse" experiment).

"Inlet" and "Outlet" refer to the point at which the odorant-containing fluid stream of each discrete odor zone enters into, and exits from, the enclosed space of the present olfactometer.

"Diverter" or "Diverting switch" refers to an element having at least two positions that enables at least two separate pathways of fluid flow. For example, when the diverter is in a first selected position, the vapor path enters an external odor chamber (containing the odorant) and a vapor now containing an odorant is permitted to pass into the olfactometer, and when the diverter is in a second position, a neutral fluid may instead bypass the external odor chamber and introduce the neural fluid to the olfactometer.

"Arena chamber" is another term for the aforesaid "Enclosed space," typically bounded by a metal floor and a glass enclosure. The glass enclosure may comprise walls and a lid in the form of a dome, creating the "enclosed space" together with the arena base plate.

"Arena base plate" refers to the arena floor. Typically there is an arrangement of openings in the arena base plate.

FURTHER SUMMARY OF THE INVENTION

The improved insect olfactometer of the current invention is a scientific research instrument and system to facilitate the study of how insects and other lower species respond to odorants. The insect olfactometer of the current invention is adapted to provide one or more "discrete odor zones" within an enclosed space. The enclosed space is bounded by a floor, one or more walls and a lid, which may be integral with the wall(s). The olfactometer has a means for inserting and releasing test subjects into the enclosed space.

In accordance with the invention, in operation the olfactometer provides one or more "defined background odor zones". The defined background odor zone allows a test subject to adjust to a constant neutral environment with baseline odor until separately approaching, or sampling, each discrete odor zone. The discrete odor zones within the enclosed space are spatially separated from each other and only accessible for a test subject to approach, or enter into, a discrete odor zone from within a defined background odor zone. In order to move from one discrete odor zone to another, the subject must traverse a defined background odor zone. An olfactometer in accordance with the current invention is not designed to employ the conventional multi-choice olfactometer design of sucking multiple odor streams into a central exhaust point where the individual odorants combine.

In use, the responses of the test subjects to the discrete odor zones are observed and statistically analyzed. The composition and concentration of the individual odor test compounds within each discrete odor zone may desirably be instrumentally analyzed for chemical composition (such as via gas chromatography-mass spectrometry, "GC-MS") to establish a quantitative chemical profile for threshold values or the concentration point at which any other responses or effects may occur.

Previous olfactometer designs introduce the individual vapor streams at distinct spatially distanced peripheral locations; however, the conventional instrumental design causes the vapor streams to merge and mix as they approach the exit of the olfactometer (typically a vacuum source at the center of the olfactometer). One or more test subjects are introduced into the olfactometer at the outlet port where the test odor(s) odorant sweep/s across the subject(s). Exposure to the test odor(s) odorant before entering the arena may alter or mask a subject's inherent response to the individual test compounds, and so he observed behavior may not accurately reflect the subject's true response to the individual test compounds. For instance, an organism may retreat from a repulsive odor on the left arm of the olfactometer and move towards the vapor stream on the right side. This could be counted as an attraction, even though the right arm vapor stream is merely neutral. The olfactometer of the current invention produces an isolated 3-dimensional space of odor for each vapor stream. Mixing and blending of vapor streams (as occurs in the traditional olfactometer design) is avoided, and a significant defined background odor zone (i.e., a neutral baseline odor environment) is also provided. This helps to prevent observations of false results.

The olfactometer design of the current invention creates discrete odor zones by incorporating paired inlet and outlet ports for each zone. The test sample odor inlet stream is directed to the outlet port which is connected to a vacuum source for removing the test sample odor along with a small amount of the background gas. This creates a clean plume of test sample vapor separate from the background and prevents mixing with the background. By utilizing individual inlet and outlet ports of this design, multiple discrete odor zones can be established within the testing chamber.

Tubing made of glass, metal, or plastic is connected to the outlet of a push-mode flowmeter. Clean air from the push-mode flowmeter may be introduced into the test chamber, and with the diverter switch the clean air can pass through an external sample chamber to introduce the sample odor to an inlet of the olfactometer. In the case of plastic tubing, new clean tubing may be used for each experiment to prevent carry-over of adsorbed odorant molecules.

The olfactometer of the current invention comprises a means of inserting and releasing one or more live organism test subjects into a defined background odor zone within the olfactometer. Desirably it also includes a means for restraining the test subject within a defined background odor zone to allow the test subject to acclimate and adjust to the environment of the defined background odor zone. A means for removing the restraint and allowing the test subject to be released into the enclosed space is also provided. This effectively confines the test subjects (e.g. insects) to an odor-free center space of the arena until the subjects are released.

In contrast, the conventional 4-choice olfactometer of prior art introduces the entrained gas or vapor odor stream via four peripheral Inlet ports. In most designs, the gas samples proceed along the parabolic baffle walls to a quadratic parabolic chamber from the side arms. Conventional insect olfactometers utilize a vacuum at the outlet port positioned at, or near, the center of the testing space (arena) which pulls the gas containing odorants from each Inlet port across the testing arena to the central gas outlet port. If all ports introduce a sample, mixing of samples will necessarily occur at near the apex of the parabolic baffle. This means that a subject in the main central space of the arena is exposed to a mixture of all the individual odor streams. A choice, or preference, for a particular odor cannot be unambiguously determined, as it will be influenced by the other odorants mixing in the central space. Simply put—the conventional olfactometer design does not provide a defined background odor zone, nor a neutral buffer zone between each odor zone, which would allow the organism to sample each odor individually. Also, instead of maintaining a clean non-contaminated arena floor with only specific areas of sample zones, the conventional olfactometer sweeps the sample over large areas of the arena floor, contaminating most of the test area.

In a conventional 4-choice olfactometer, the test subject is introduced at the central gas outlet port and is generally exposed to the sweeping gas mixture. With this setup, the test subject is initially subjected to a mixture of up to four samples, or four different odorants, before responding to the desired isolated test compounds being introduced at each side Inlet port. This conventional design does not provide for an odor-free acclimation period, making the determination of threshold values difficult.

Also, the complex shape of the conventional design limits its economical construction to plastic and, to be cost effective, the height of the arena chamber is generally limited to less than two inches. Since all the gases exit at only one port, a larger volume (larger sized olfactometer) only increases diffusion, which enhances mixing. The limited height makes the conventional olfactometer ineffective for larger flying insects.

Design of the Current Invention

The testing arena of the olfactometer of the current invention comprises one or more gas outlet ports, which may be in the form of "manholes" strategically placed in the testing floor (arena base plate). In an exemplary embodiment of the invention implementing a "coaxial design," the fluid odorant streams enter the arena through inlet tubes or pipes that protrude into the enclosed space through each outlet port. Each inlet port tube (protruding though an outlet port) can be height-adjustable (fountain height) for optimizing the stimulus cloud pattern of the discrete odor zone, for either flying or crawling subjects.

In an exemplary embodiment implementing an "air fountain design," such an olfactometer of the current invention has an inverted loop flow. For example. a bell-shaped glass impinging cap can be affixed to the top of a glass stem for redirecting the gas flow downward and parallel to the outlet port This collineated design ensures a controlled diffusion boundary around each outlet port, enabling the four ports to introduce sample without mixing with the test chamber air within the defined background odor zone.

In a preferred design, the inlet tubes can be moved in and out to lengthen or shorten the height of the discrete odor zone. Note that different shapes of caps can be used for collineating a longer path length. This unique design creates an isolated periphery zone (cloud) around each of the inlet ports, extending towards the corresponding outlet ports creating something like a fountain at each port. Thus, a "plume" or column (a discrete odor-zone) is created within the enclosed space of the olfactometer. By constructing four separate inlet/outlet pairs within a single enclosed olfactometer testing space, it is like having four separate air fountains (discrete odor-zones) from which to choose and by simply changing the diverting switch, a test sample from any fountain can be interrupted and clean air can once again pass through the Inlet port.

In preferred embodiments of the present invention, the discrete odor zones may generally be cylindrical, conical, or barrel shaped; wherein, if conical, the wider diameter is towards the outlet end, and the narrow end may be truncated. In general, the discrete odor zones may have any shape; however, in preferred embodiments, the cross-section of each discrete odor zone is more-or-less circular. Other shapes can be generated by using shaped inlet and outlet ports (oblong, air-curtain, etc.). Discrete odor zones with more complex shapes (such as Y or X-shaped) can be generated by using multiple inlets and outlets for each zone, or by incorporation of baffles or diverters. The orientation and direction of each odor zone may be in any direction (vertical, horizontal, diagonal, up, down, left, right, etc.). The discrete odor zones will generally be partially, or fully-surrounded by a defined background odor zone; The boundaries of the discrete odor zones may also be partially determined by the walls or perimeter of the enclosed space The discrete odor zone may also be a "blank" zone, wherein the composition of the discrete odor zone is identical to the defined background odor zone—for instance the discrete odor zone may be missing a component of the defined background odor zone (a "reverse" experiment).

In an exemplary embodiment of the olfactometer, a vertical glass inlet tube is inserted through a fitting on the bottom of a glass insect-collecting trap. This fitting permits the stem to be adjusted up or down for optimizing the test plume to the type of subject under study. Crawling insects generally require a lower stem height and flying insects generally a higher stem height. The glass Inlet tube may be coaxially aligned through the outlet port and slid along its axis to adjust the stem height.

The other port on the insect trap is connected to the vacuum manifold (each of the four traps is connected to the manifold). The outlet port manifold is connected to the pull port (vacuum) on the air exhaust system. It is desirable that the sum of gases evacuated be slightly greater than the total input thereby allowing some excess air to enter the test chamber through the central insect release tube. This ensures a sweeping laminar current of fresh air from the center to all four outlet ports and prevents back diffusion to the acclimating space.

Although the olfactometer of the current invention does not rely on a central outlet port, it may be useful in some cases to incorporate such a port into the design. This can be useful for flushing or purging the olfactometer between experiments, or to allow the olfactometer to function in "conventional mode" if desired—such as for making comparisons to data collected using other conventional systems.

The size, shape, position, uniformity, and intensity of each discrete odor zone of the olfactometer is established by the construction parameters (size, position, and geometry of inlet and outlet ports) and operating conditions (such as gas flow rate and pressure and would generally not be visible to an observer. However, the discrete odor zones can be "mapped" by various methods either prior-to or during use. This may be done to ensure that each odor zone remains discrete, and does not overlap other odor zones, or the odor-free neutral zone. Perhaps the simplest method is to use visible smoke to view the shape and position of the discrete odor zone. Commercial smoke products that are available for similar purposes can be used.

Some odorants may be observable by spectroscopic means such as UV or infrared-red (IR) beams. Radioactive tracers can also be used. The "wall" (boundary) of a discrete odor zone could be visualized by utilizing a reaction of two different airborne chemicals which produce a visible product when they intersect.

Gas-sampling capillaries may be installed and connected to sensitive GC/MS instruments. The tips of the sampling capillaries can be moved and positioned in a precise manner to generate a position/intensity map of the molecular plume of each discrete odor zone.

Less-sophisticated methods may also be used. For example, damp litmus paper placed at various positions in the enclosed space can be used to measure the presence or absence of acidic or basic odorants such as ammonia or acetic acid. Thermal imaging may also show the air flows by introducing cold or hot gases in the inlet tubes. It is expected that various similar-sized molecules will produce odor zones having identical shapes, thus the visualization of the odor zone established using one kind of molecule is expected to be valid for other molecules, as long as the physical parameters of the olfactometer design and operating parameters remain constant. The outlet ports of each discrete odor zone may be connected to collection traps for volatiles to collect and analyze the total amount of odorant delivered over a set period of time.

The external odor-generation chambers of the olfactometer can be daisy chained into a variety of combinations for testing. This provides for testing various blends. If one wishes to change concentrations, an external mixing chamber is employed. This will require an auxiliary gas delivery system whereby one or more components (the concentrate) is mixing with a diluting gas to create the desired concentration for introduction. Multiple mixing chambers with the appropriate gas proportionating delivery system facilitates varying concentrations of a sample for testing at each inlet port.

The olfactometer may also comprise a changeable arena base plate. A preferred arrangement is four equally spaced 1.19" diameter holes on a 3" radius; however, the pattern, hole size, and number of tubes (choices) can be as many as desired, limited only by size and practical considerations.

Glass traps may be inserted into the base stand and sealed with the base plate. An all-glass acid-etched base arena can be employed. Each separate odor-mixing chamber can introduce a changing concentration of one or more components or blends to any inlet port of the olfactometer.

The olfactometer may incorporate a diverting switch at each outlet port of the flowmeter on the clean air flow system, resulting in two ports for each exit from the flow meter. This allows clean air into the olfactometer enclosed space Inlet port—or by changing the switch position, the airflow can be diverted to an external reservoir for inserting and releasing the test sample (odorant) to the chamber Inlet port. Since each of the flowmeters may have a diverter, any chamber Inlet port can be activated with an odor or deactivated back to clean air, all without disrupting the overall (total) air flow into the test chamber. All test chamber Inlet ports preferably begin with the diverter positioned to the clean air mode to establish a baseline, non-biased, stimulus-free environment for acclimating the subjects to their new condition before switching to the stimuli mode.

Each of the four inlet ports desirably incorporates this diverting feature, allowing the researcher maximum flexibility as to when and in what combination the samples may be introduced into each of the four inlet ports. This improvement allows the user to easily turn on a stimulating inlet port (sample introduction) and, on the fly, turn the stimulating inlet port off (and still have odor-free air delivered at the same rate) It is an aspect of this invention that the olfactometer comprises one or more gas diverter switches.

The olfactometer is designed for maximum flexibility and reproducibility in olfactometry research; however, its novel design is not limited to olfactometry. Light, heat, magnetic fields, electric fields, and sound stimuli can also be introduced either separately or in simultaneous combinations to fully understand how organisms respond to the real natural world.

It has been shown that insects may respond to some odorants at concentration levels as low as 10 ppm. This type of sensitivity mandates a procedure for scrupulously cleaning the apparatus after each experiment to ensure no residue or accumulation of compounds on the testing surface, i.e., to prevent a memory effect. As previously stated, the insect response may be a change in walking patterns, a change in flight patterns or more commonly an attraction toward the test sample (compound) or an avoidance away from the test sample.

A small amount of the test sample(s), although in the gas phase, upon impact with the surface of the chamber may still adhere to the surface. Plastics, even though chemically inert, are generally organic polymers, and substances can often get imbedded into the surface. Over time and repeated use, odorant compounds can continually build up on the plastic surface. If not removed, eventually the out-gassing level from the polymer will create the problem of a memory effect.

Unfortunately, rigorous cleaning is not possible with plastics. This slow, unpredictable outgassing will introduce a bias in future experiments. A glass-metal system permits standard rigorous cleaning procedures, i.e., high temperatures, autoclaving, chemical treatment, UV, etc. to ensure removal of surface contaminants. It is a feature of the current invention that the insect olfactometer system is designed such that all internal surfaces may be either glass, metal, or ceramic, facilitating proper cleaning protocols.

A major consideration in living response systems for olfactometry is a clean air source, such as the clean air delivery systems manufactured by Sigma Scientific, LLC (Micanopy, Fla.). The most common system for the olfactometer set-up will be a four-choice push-pull (pressure/vacuum) set up.

As the name implies, the clean air delivery system does just that. Standard compressed air is put into the system whereupon after centrifugation (large particle removal) and coalescing (aerosol removal), the air pressure is monitored and regulated. This regulated air then enters a four-port manifold where each port is connected to a special carbon filter (volatile removal) linked to a flow meter that precisely controls the flow of the now-clean air for introduction at each Inlet port through the base plate arena of the olfactometer.

The olfactometer of the current invention has been designed to study insects, and the prototype devices have been constructed to the appropriate scale (approximately a one cubic foot enclosed space). However, one skilled in the art will realize that the same principles, features, and aspects can be used to produce olfactometers of any size, such as micro-scale devices to study single cell organisms, or very large (room-sized) olfactometers for use with large mammals such as human beings. The olfactometer should be sized according to the size, number, and mobility of the test subjects. For example, flying insects will generally require a larger space (area and height) than slow-crawling insects. Large beetles will require a larger design than for dust mites. The size of the olfactometer should allow for at least approximately 5 to 10 body lengths between the central point and the front of each discrete odor zone for walking of crawling subjects, and larger for flying organisms. Slow or immobile subjects, such as plants, sea anemones or bacteria require less distance.

Body length refers to the horizontal distance—for example, a six-foot-tall human is only approximately 2 feet wide in the direction of travel. Thus, an appropriate size range for human subjects would be approximately 10 to 20 feet between the central point and the front of each discrete odor zone. A 10-foot snake has a head only 6" in size, so a distance of 30" to 60" between the central point and the front of each discrete odor zone might be appropriate.

For insects 1 cm in length, a distance of 5 to 10 cm would be appropriate. Adding-in the dimensions of the discrete odor zones (approximately ⅕ to ⅓ times the distance between the central point and the front of each discrete odor zone), plus a buffer zone along the wall, an overall floor size of approximately 100 to 1,000 cm² would be appropriate for 1-cm insects. Accordingly, the size range for the base footprint of the enclosed space for a preferred embodiment of this invention is between 100 and 1,000 cm². For larger, smaller, or greater numbers of test subjects, the optimum size could differ by over one order of magnitude. Optimum height will be at least 1.5× the height of the test subject for walking, crawling, or stationary subjects, and at least 10× for flying test subjects.

The concepts concerning the olfactometer design are not limited to the gas phase. A similar procedure may also be performed in the liquid state such that the carrier could be water which is entrained with the desired odorant. The test chamber is then similar to an aquarium which contains the test subjects (such as fish or swimming insects) that respond to the components within a defined liquid slip stream.

The olfactometer of the current invention comprises an enclosed sealable space, or chamber, within the olfactometer, wherein said enclosed space comprises a defined background odor zone.

The olfactometer of the current invention comprises a means of inserting and releasing at least one live organism test subject into a defined background odor zone within the olfactometer.

The olfactometer of the current invention comprises a means of generating one or more discrete odor zones within the olfactometer, while also still maintaining a defined background odor zone within the olfactometer.

The olfactometer of the current invention comprises a means for visual observation of the interior of the enclosed sealable space of the olfactometer.

The olfactometer of the current invention comprises a means of generating one or more discrete odor zones within the olfactometer, wherein said means comprises a multi-way switch or diverter that controls the flow of a pressurized gas or vapor stream.

In preferred embodiments of the olfactometer, one or more discrete odor-zones are evenly distributed around defined background odor zone within the enclosed space.

In preferred embodiments, there are four discrete odor-zones within the enclosed space of the olfactometer.

In preferred embodiments, the means for generating a discrete odor zone comprises an inlet to deliver a gas or vapor, and an outlet to remove the gas or vapor, wherein said inlet and outlet are positioned to maintain a discrete odor zone within the enclosed space of the olfactometer, and the size, shape, position, uniformity, and intensity of said discrete odor zone is established by the size, position, and geometry of said inlet and outlet, and the gas flow rate and pressure of said gas or vapor.

In preferred embodiments, the inlet and outlet comprise holes, ports, tube, or pipes.

In preferred embodiments of the olfactometer, the inlet comprises an inner tube or pipe that has a smaller diameter than the outlet, and the inlet tube or pipe is routed inside, within, or protrudes through a larger-diameter outlet port.

In preferred embodiments, the position of the terminal end of the inlet tube or pipe can be adjusted longitudinally along the axis of the inlet tube or pipe to control the distance between the inlet and outlet ends of the discrete odor zone.

In preferred embodiments, the terminal end of the inlet comprises a baffle or bell-shaped cup, or impinging cap, to re-direct the flow of inlet gas towards the outlet, or to promote laminar flow of the gas stream. The terminal end of the inlet may also comprise a screen, frit, or other porous barrier to prevent test subjects (such as flying insects, for example) from entering the inlet In preferred embodiments, a negative pressure or controlled vacuum is applied downstream from the outlet in order to draw the gas or vapor odor stream out of the enclosed space.

In preferred embodiments, all interior surfaces of the olfactometer are constructed of metal, glass, or ceramic.

In preferred embodiments, the outlet for the discrete odor zone is a hole positioned on the bottom floor of the enclosed chamber of the olfactometer; wherein said hole is large enough for the live organism test subject to enter.

The olfactometer of the current invention comprises a trap downstream from the outlet of the discrete odor zone; wherein, live organism test subjects can enter said trap and be prevented from re-entering the test chamber.

In an exemplary embodiment, the floor of the enclosed chamber has a roughened surface to provide traction and facilitate the mobility of walking or crawling organisms. In an alternative embodiment, the floor of the enclosed chamber is fitted with a removable insert constructed of metal, cellulose, fiberglass, or paper to provide traction, and facilitate the mobility of walking or crawling organisms. The removable insert also aids in cleaning the device between uses. The removable insert may be of a preferred color or texture (matt-sponge like) for mimicking the preferred environment of the test subject.

It is s feature of the olfactometer that the means for inserting and releasing live organism test subjects desirably comprises a means to hold the subject within an odor-free neutral zone until a chosen start time for the olfactory-choice test.

It is a feature of the olfactometer of this invention that means for inserting and releasing live organism test subjects comprises an inlet for supplemental odor-free gas or vapor to enter the enclosed chamber. In a typical embodiment of the invention, the enclosed space of the olfactometer has a base footprint between 4 and 10,000 cm$^2$, and a height between 2 and 100 cm. In preferred embodiments of the invention, the enclosed space of the olfactometer has a base footprint between 100 and 1,000 cm$^2$, and a height between 10 and 50 cm.

In a typical embodiment of the invention, the olfactometer has between 2 and 10 discrete odor zones evenly-spaced around a central defined background odor zone; In preferred embodiments of the invention, the olfactometer has between 2 and 6 discrete odor zones; and in a most preferred embodiment of the current invention, the olfactometer has 4 discrete odor zones.

It is a feature of this invention that a test subject may freely move about within the enclosed space.

It is a feature of this invention that the enclosed space may comprise barriers to restrict the subject's access to the whole of the enclosed space.

It is a feature of this invention that fixtures such as perches, ledges, landing pads, grids, and the like, may be placed within or adjacent to each discrete odor zone in order to provide the test subject a place to sit or rest after being attracted to said zone. For example, a screen may be placed within a discrete odor zone, so that flies may land on the screen after being attracted.

BRIEF DESCRIPTION OF THE DRAWINGS

FIG. 8A shows an introduction tube in the opened condition. FIG. 8B shows the introduction tube in the closed condition. [Insect release device]

DETAILED DESCRIPTION

Figure 1:
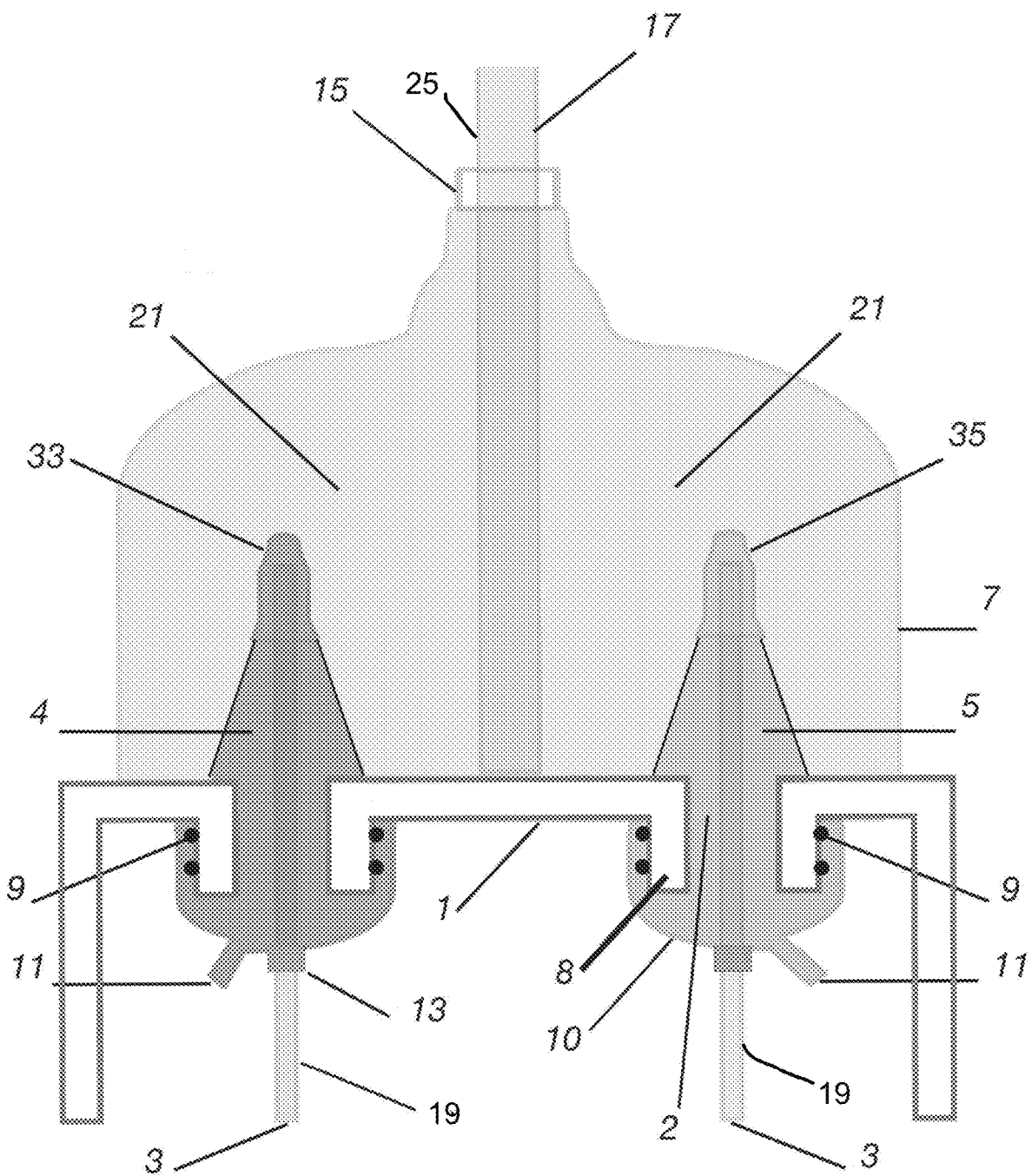
FIG. 1 is a schematic diagram of the elevation-view cross-section of an olfactometer of the present invention depicting two of the discrete odor zones with the coaxial (fountain) flow design. Suggested title (Coaxial flow olfactometer-flying insects)

Turning to FIG. 1, this schematic diagram of a typical coaxial embodiment of the olfactometer shows the arena base plate 1. In the arena base plate 1, there are two (or more) outlet ports 2, through which extends coaxially a pair of Inlet tubes 19. Each Inlet tube 19 allows a different vapor stream to pass into the enclosure 21 during operation of the olfactometer. Shaded areas 4 and 5 depict two different discrete odor zones. A glass enclosure dome 7 serves as the wall and lid of the olfactometer. The background, or neutral, odor zone is depicted at 21.

A pair of O-ringed stubs 8 extend from outlet 2 openings in the bottom of the base plate 1. A pair of O-rings 9 grip the O-ringed stubs 8. Each of the O-rings 9 secures the insect trap 10.

Glass insect traps 10 extend from below the arena base plate 1. Each of the glass insect traps 10 has a vacuum outlet arm 11 in for withdrawing the gases from the olfactometer.

An inlet tube 19 extends coaxially through each of the insect traps 10. A threaded adapter 13 allows for height adjustment of the inlet tube. A set of bell-shaped deflector caps 35 cause the rising flow of fluid (vapor) to be deflected downwards, forming each of the discrete odor zones 4,5.

In this embodiment, living test organism(s) are introduced through an insect release tube 17, which passes through a sealing cap 15.

Figure 2:
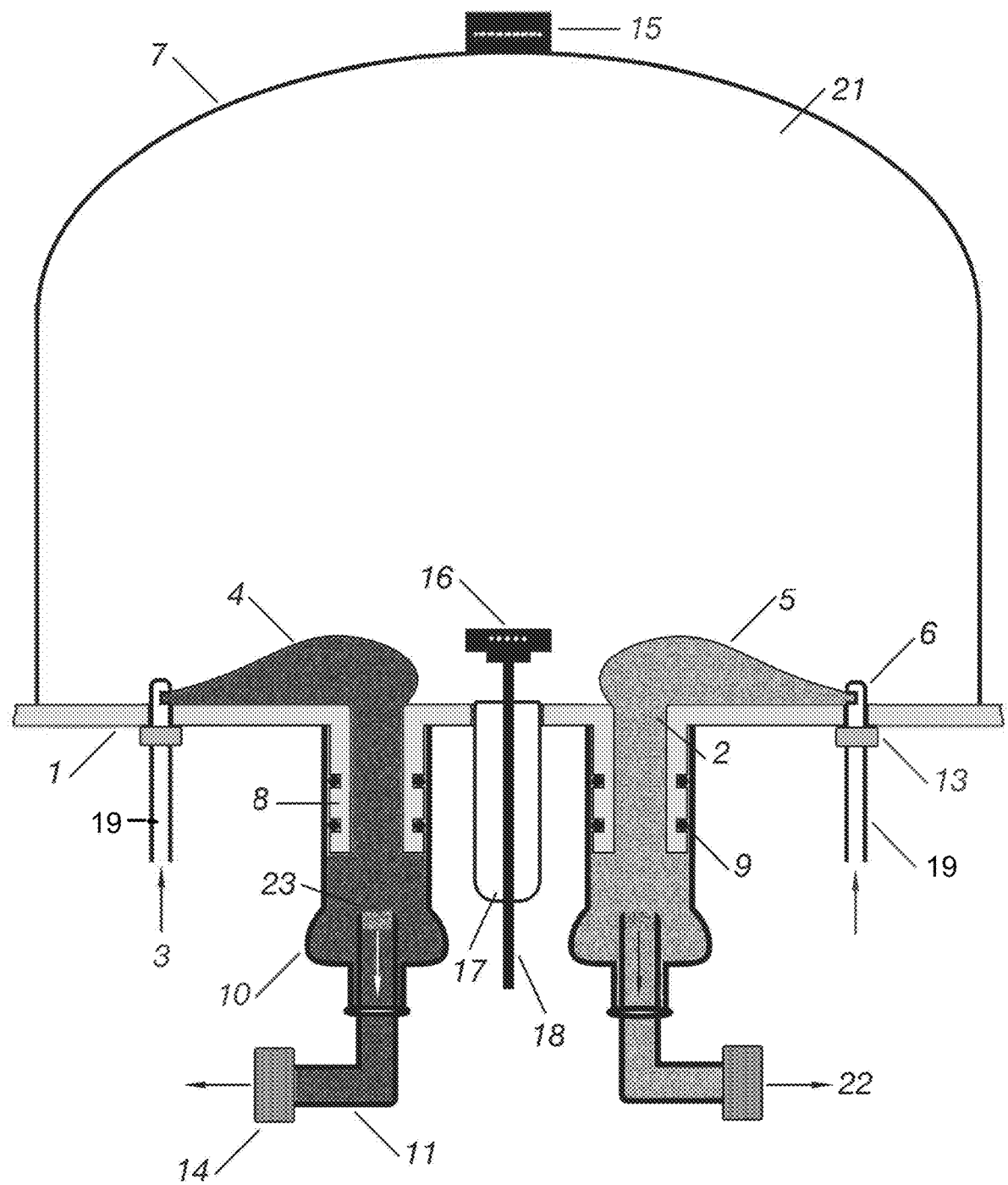
FIG. 2 is a schematic diagram of the elevation-view cross-section of an olfactometer of the present invention for crawling insects, depicting two of the discrete odor zones with adjacent cross flow design. Suggested title (Coaxial flow olfactometer-crawling insects)

FIG. 2 shows a schematic diagram side view cross-section of a typical crawling insect embodiment of the present olfactometer, with adjacent inlet tube 19 for fluid(vapor), each containing a test odorant or a neutral control.

The arena base plate 1 has outlet ports 2 from which integral O-ringed stubs 8 & 9 extend downward with that serve to secure glass traps 10 thereto. For each discrete odor zone, an Inlet tube 19 extends from below the arena base plate 1 to deliver odorant-containing fluid (vapor) or neutral (vapor)into the enclosure through a slit at the end of each Inlet tube 19, which faces a corresponding outlet port 2. This arrangement produces the individual flow profiles depicted as discrete odor zone 4 and zone 5 for crawling subjects. 7 is the glass dome enclosure. 8 is the O-ring stubs off the bottom of the base plate. 9 is the O-ring. 10 is the glass insect traps. 11 is the vacuum adapter. 12 is the inlet tube. 13 is the loosening nut for raising or lowering the inlet tube. 14 is the tightening nut for the vacuum. 15 is the screened vent. 16 is the specimen closure cap. 17 is the glass specimen tube. 18 is the specimen release rod. 21 is the background odor zone, 22 is the vacuum port. 23 is the glass frit on the vacuum adapter.

Figure 3:
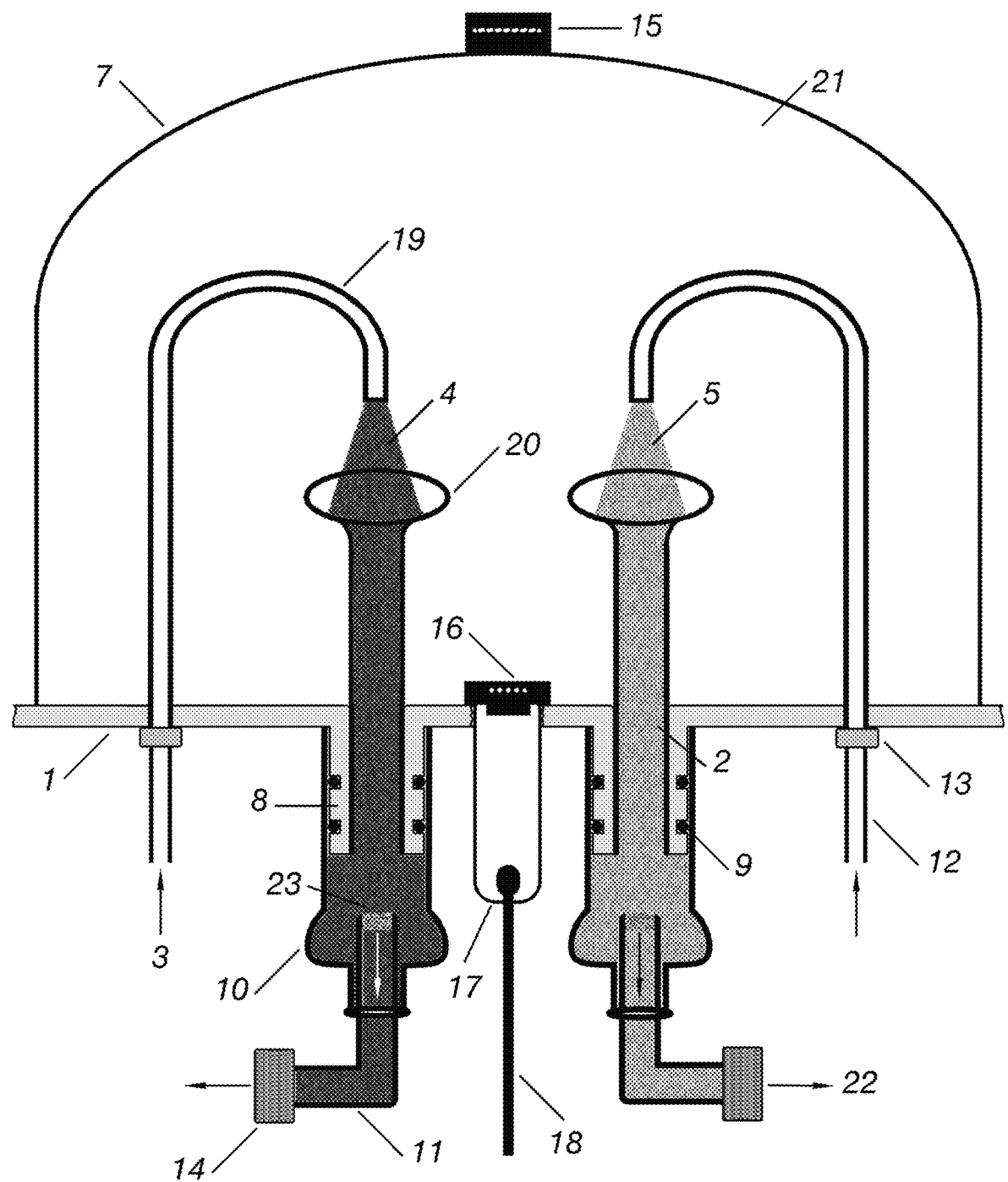
FIG. 3 is a schematic diagram of the elevation-view cross-section of an olfactometer of the present invention for flying insects with adjacent (shower head) flow design. Suggested title (Adjacent flow olfactometer-flying insects)

FIG. 3 is a side view cross-section schematic diagram of a typical flying insect embodiment with adjacent inlet tube 19 and flying insect adapters 20 for the olfactometer. 1 is the base plate. 2 is the outlet port in the base plate. 3 is the opening of the inlet tube. 4 and 5 are shaded areas representing two different discrete odor zones. 7 is the glass dome enclosure. 8 is the O-ringed stubs on the bottom of the base plate. 9 is the O-ring/s. 10 is the glass insect trap for "J" type inlet tubes 19. 11 is the vacuum adapter. 13 is the loosening nut for raising or lowering the inlet tube. 14 is the tightening nut for the vacuum connection. 15 is the screen vent. 16 is the specimen closure cap. 17 is the glass specimen container. 18 is the specimen release rod. 19 is the "J" shaped inlet tube. 20 is the glass flying insect adapter. 21 is the background odor zone. 22 is the vacuum outlet port. 23 is the glass frit on the vacuum adapter.

Figure 4:
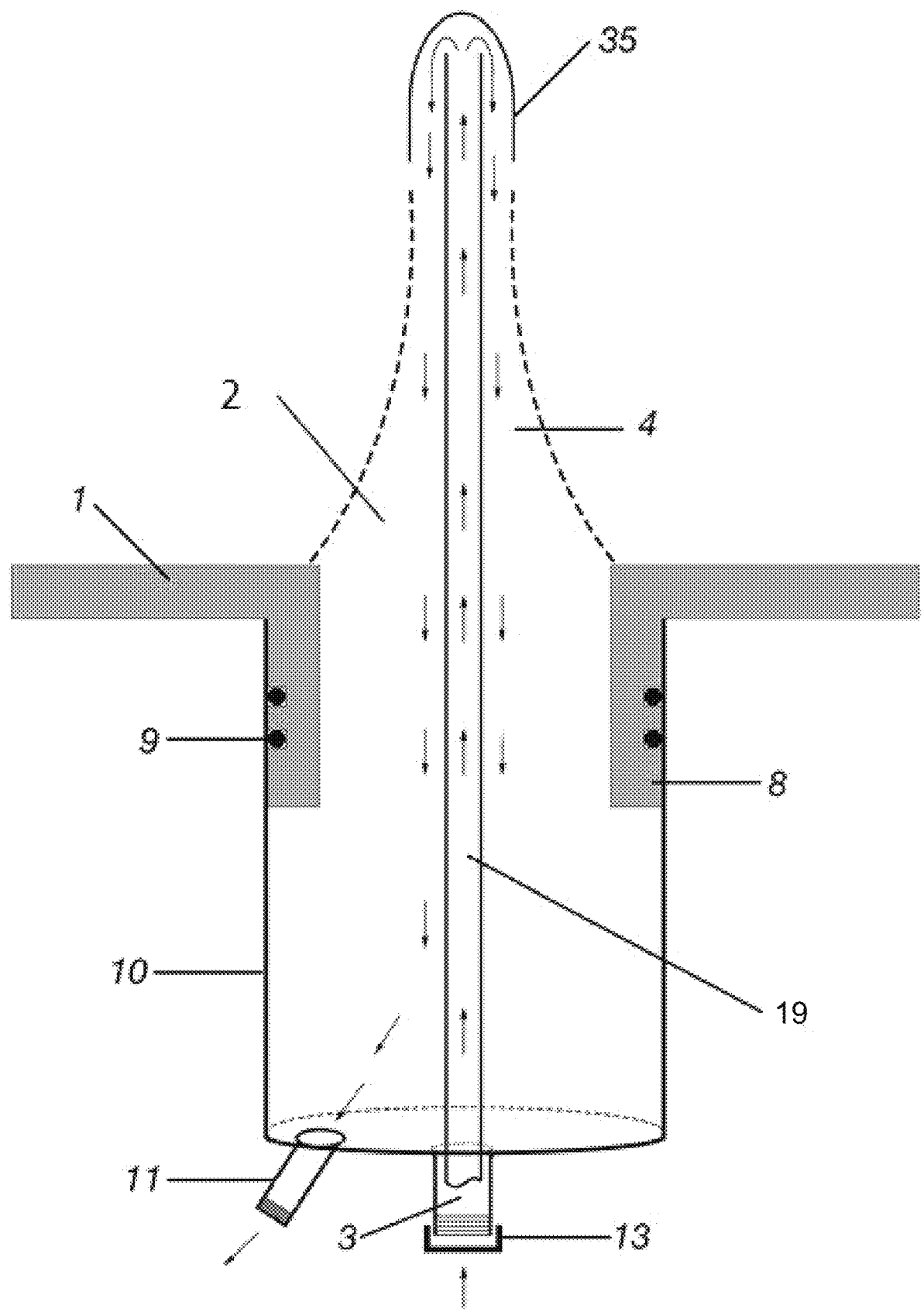
FIG. 4 depicts the flow pattern of the olfactometer for the co-axial (fountain) design of FIG. 1, along with the manner of sealing the glass traps to the stubs. It shows the connections of the glass traps, sealing plate, aligning plate, glass enclosure, and stand within the olfactometer. [Detailed coaxial flow pattern.]

FIG. 4 is a cross section of the operative elements of a coaxial flow design implementing the present invention. A discrete odor zone 2,4 is outlined by dashed lines. The opening 3 of the Inlet tube 19 conveys a stream of fluid upwards until it is deflected downwards and outwards by a bell-shaped deflector 35.

The base plate 1 supports a stubbed port 8 that acts as a stub for large O-rings 9 onto which a glass insect trap 10 is fitted to provide for coaxial flow through the Inlet tube. Exit of fluid is through a vacuum outlet arm 11. A threaded arm 13 allows for height adjustment of the inlet tube.

Figure 5:
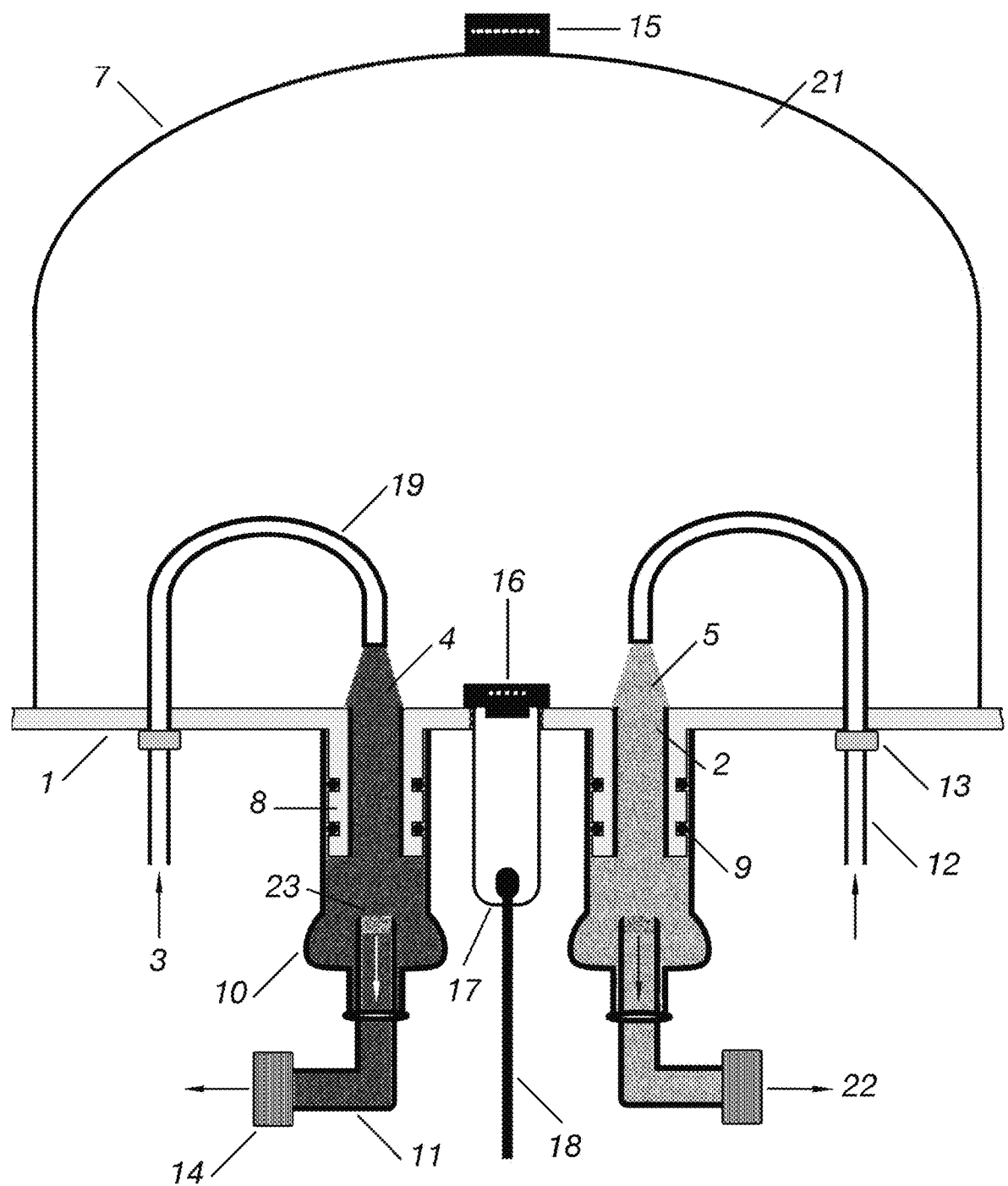
FIG. 5 is a schematic diagram of an olfactometer similar to FIG. 3 but adapted for use with crawling insects. [Adjacent flow olfactometer-crawling insects.]

FIG. 5 is a cross section of an olfactometer of the invention in the showerhead ("J") flow design without the flying insect adapters. The glass dome enclosure 7 has a screened vent 15 at its top. The arena base plate 1 has a plurality of outlet ports that include O-ringed stubs 8 which communicate with the enclosed space above the plate 1 and which support large O-rings 9 that hold glass specimen traps 10 below the arena.

Figure 6:
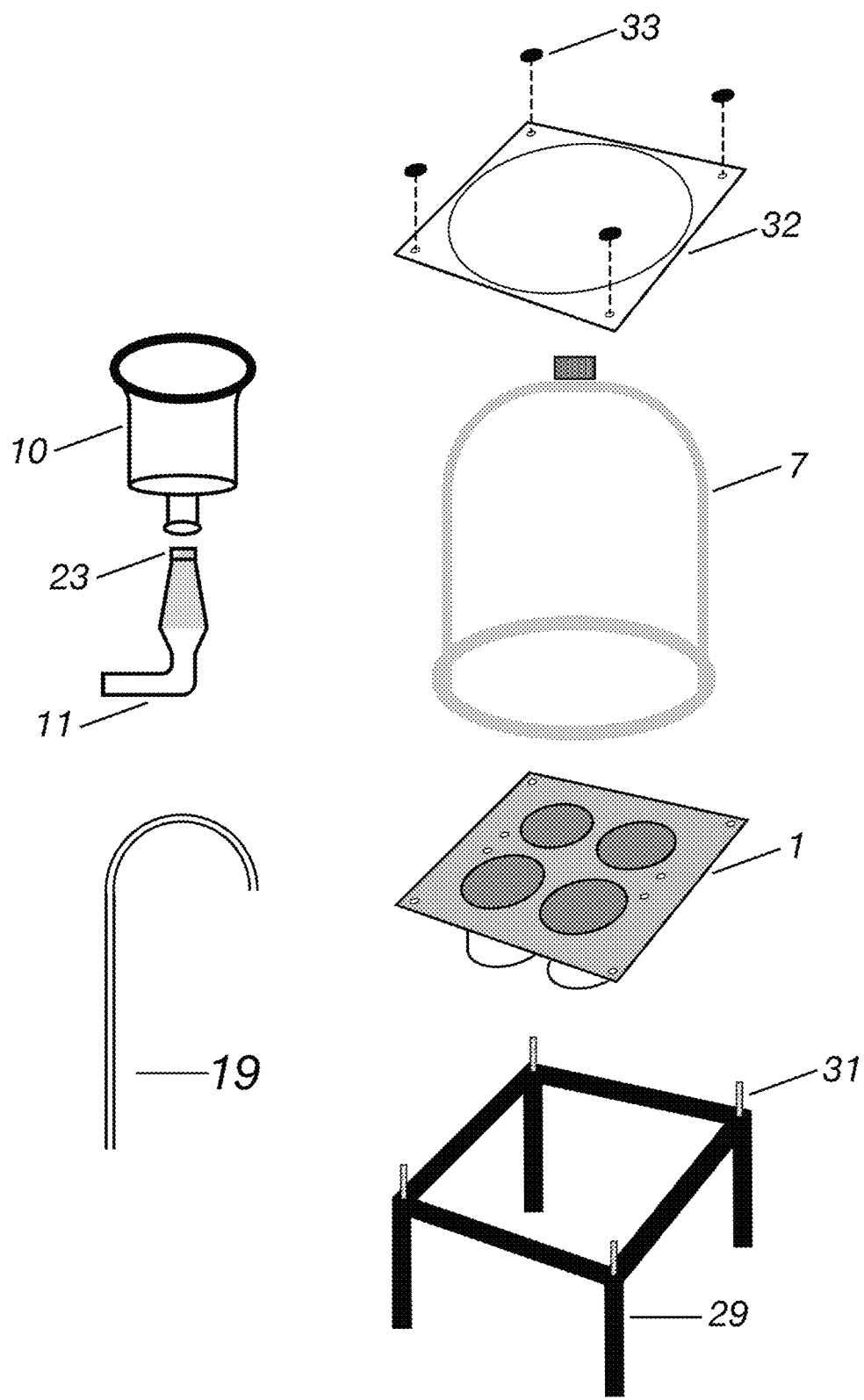
FIG. 6 is an exploded, assembly array view of an olfactometer of the present invention embodying the adjacent (shower head) design, providing views of the glass traps, arena base plate, aligning plate, glass enclosure, and stand. [Assembly of adjacent flow olfactometer.]

Two different discrete odor zones 4 and 5 are depicted in this cross-section view, although there would typically be four of them as implied in FIG. 6.

A glass specimen container 17 provides a means for introducing a live test organism by pushing specimen release rod 18 and dislodging specimen closure cap 16, allowing the organism to enter the center of the arena in a neutral background zone 21.

Tube 19 provides an opening for flow of fluid containing test odorant or neutral vapor into the enclosed space. Nuts 13 secure the J Inlet tubes 19 to the arena base plate 1 and allow for adjusting the height of the Inlet tubes that are threaded on the outside.

Specimen traps 10 are mounted below the arena via the O-ring stubs 8. Each of the specimen traps 10 is connected in communication with a vacuum outlet arm 11 terminating at a threaded pipe tightening nut 14 for vacuum connection. The inlet of the arm 11 is protected by a fritted glass filter 23.

FIG. 6 is a schematic assembly array for the olfactometer for the adjacent mode (showerhead). The olfactometer stand 29 has aligning studs 31 extending therefrom. The arena base plate 1 has stubs with large O-rings. The glass dome 7 forms a wall and lid of the chamber enclosure. The dome aligning plate 32 is secured with knobs 33 for fastening it to the stand 29. One of the glass traps 10 is depicted in unassembled condition, where a vacuum adapter 11 has a porous glass frit 23. Each of the J shaped inlet tubes 19 is to be installed through a hole in the arena base plate 1.

Figure 7:
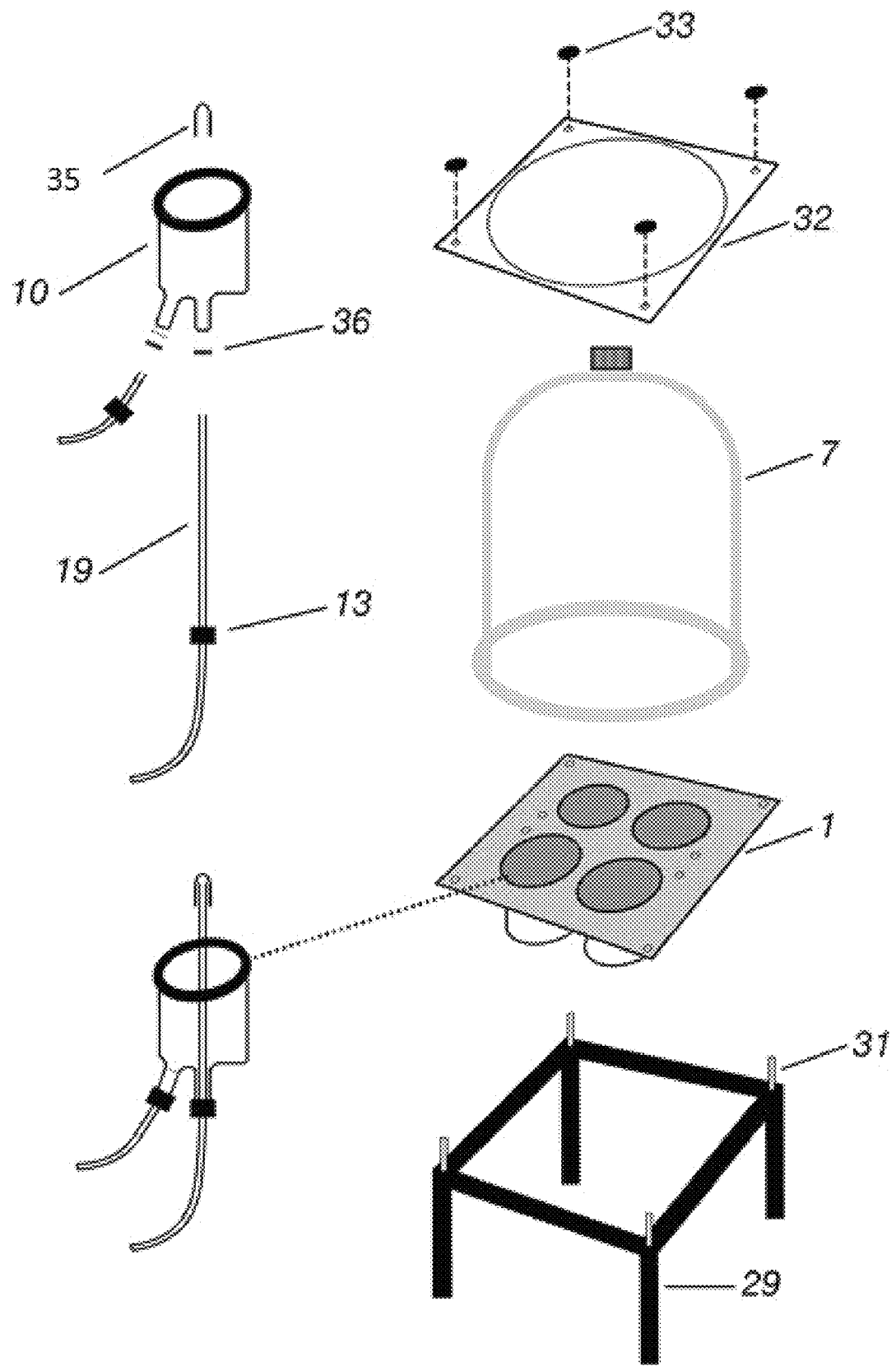
FIG. 7 is an exploded, assembly array view of an olfactometer of the present invention similar to FIG. 6 but embodying the coaxial (fountain) flow design. [Assembly of Coaxial Flow Olfactometer.]

FIG. 7 is a schematic assembly array for the olfactometer for the coaxial mode (fountain). The olfactometer stand 29 supports the arena base plate 1, with O-ringed stubs. A glass dome 7 is secured in place by a dome aligning plate 32, via tightening knobs 33. An exploded view of the assembly for one of the glass traps 10 is shown above an assembled view, the latter of which points to where one of the glass traps 10 would be placed when in use. A tightening nut 13 on the inlet tube 19 is for height adjustment. The bell diverter 35 is shown at the top of the exploded diagram of the glass trap assembly. Small O-rings 36 secure the tubes to the glass trap 10.

Figure 8A:
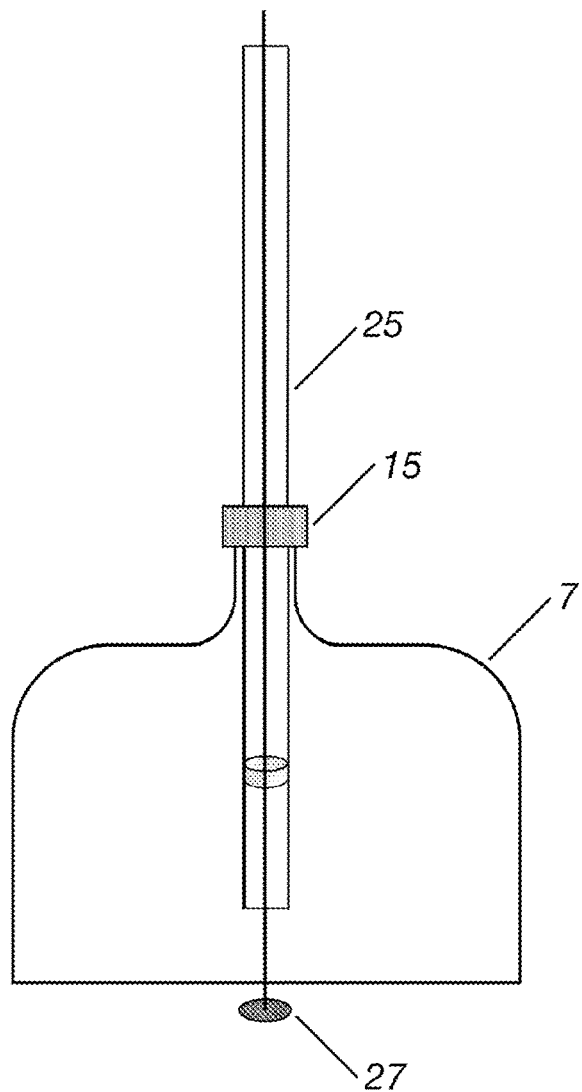
FIGS. 8A and 8B depict a schematic diagram of a means for introducing test organisms into an olfactometer of the present invention.
Figure 8B:
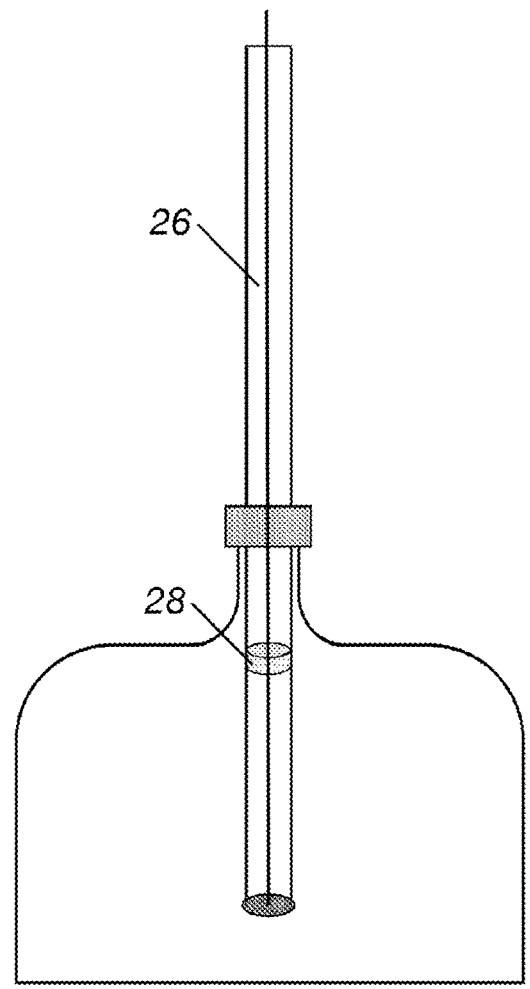

FIG. 8 shows the design and function of a means for introducing test organisms into the olfactometer. On the left is shown the "open" release condition, and on the right is the "closed" holding state. The test organism is released by lowering the pushrod 26 on the release tube 25, opening the retaining screen 27. Element 28 is a porous bearing, and element 15 is a cap through which the release tube extends.

Figure 9:
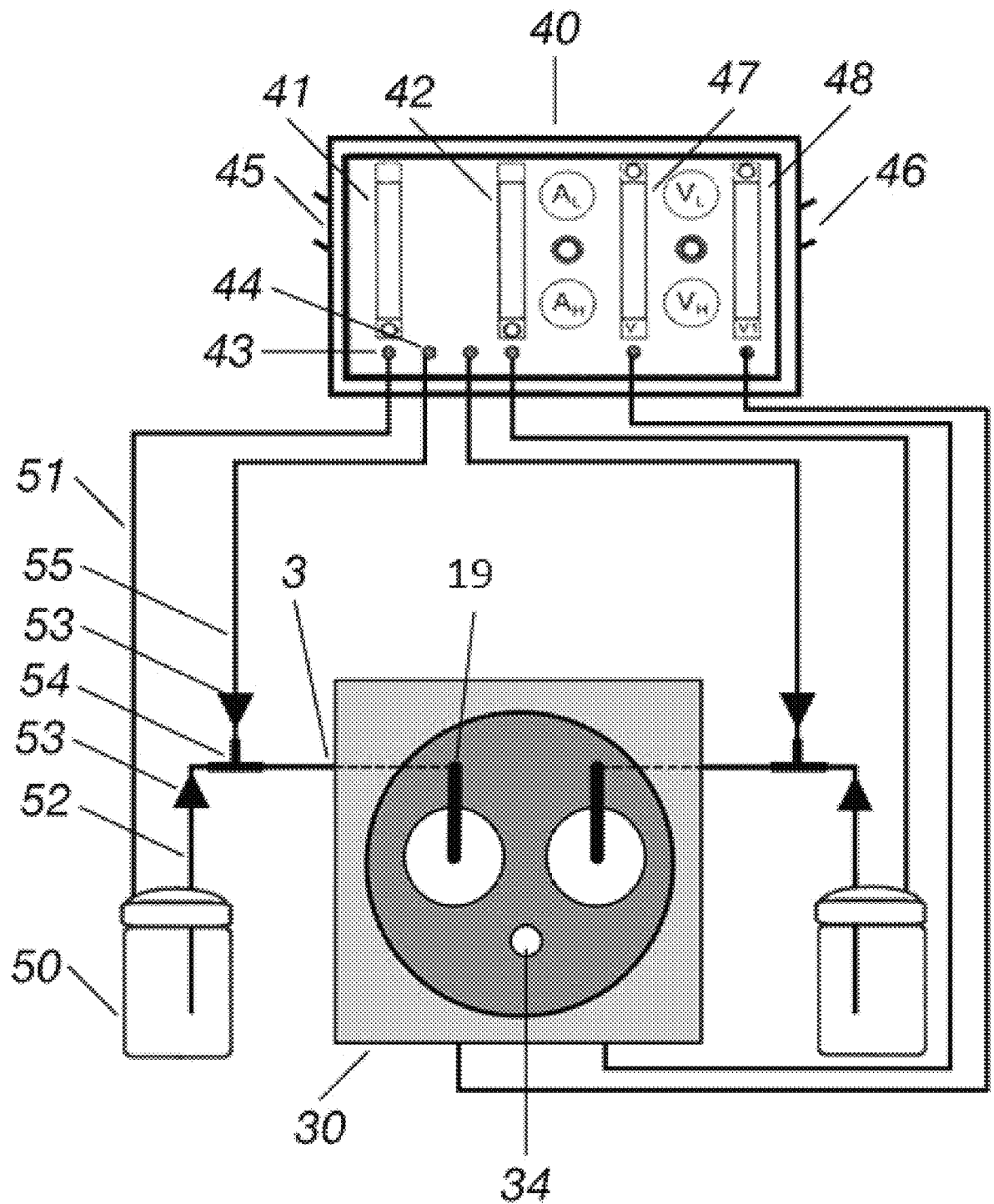
FIG. 9 is a schematic of an olfactometer of the present invention embodying the adjacent (showerhead) design along with the external odor chambers and air delivery system. [Complete assembly of adjacent olfactometry system]

FIG. 9 is a schematic of the complete assembly of the olfactometer in the adjacent (showerhead) mode. 1 is the arena base plate. 3 is the connector tube which connects the tee 54 to the "J" shaped inlet tube 19. A clean air line 55 extends from the air delivery flowmeter to the check valve 53 adjacent to a tee connector 54. A glass external odor chamber 50 has a lid from which two pipes 51, 52 exit. Line 51 connects the air from the air delivery system flowmeter 43 to the inlet 51 of the external odor chamber. Line 52 connects the outlet of the external odor chamber to the check valve 53. The air delivery system 40 includes an outlet flow meter (pressure) 41 for testing port one. The outlet flowmeter (pressure) 42 is for testing port two. The outlet 43 from the pressure flowmeter is shown in the odor mode position. The outlet 44 from the pressure flowmeter is in the clean-air-only mode position. Divertor switches 45 are for the pressure flowmeters 41,42. The vacuum flowmeter 47 is for testing port one. The vacuum flowmeter 48 is for testing port two. On/off switches 46 are for the vacuum flowmeters 47,48. The specimen release port 34 is in the base plate.

Figure 10:
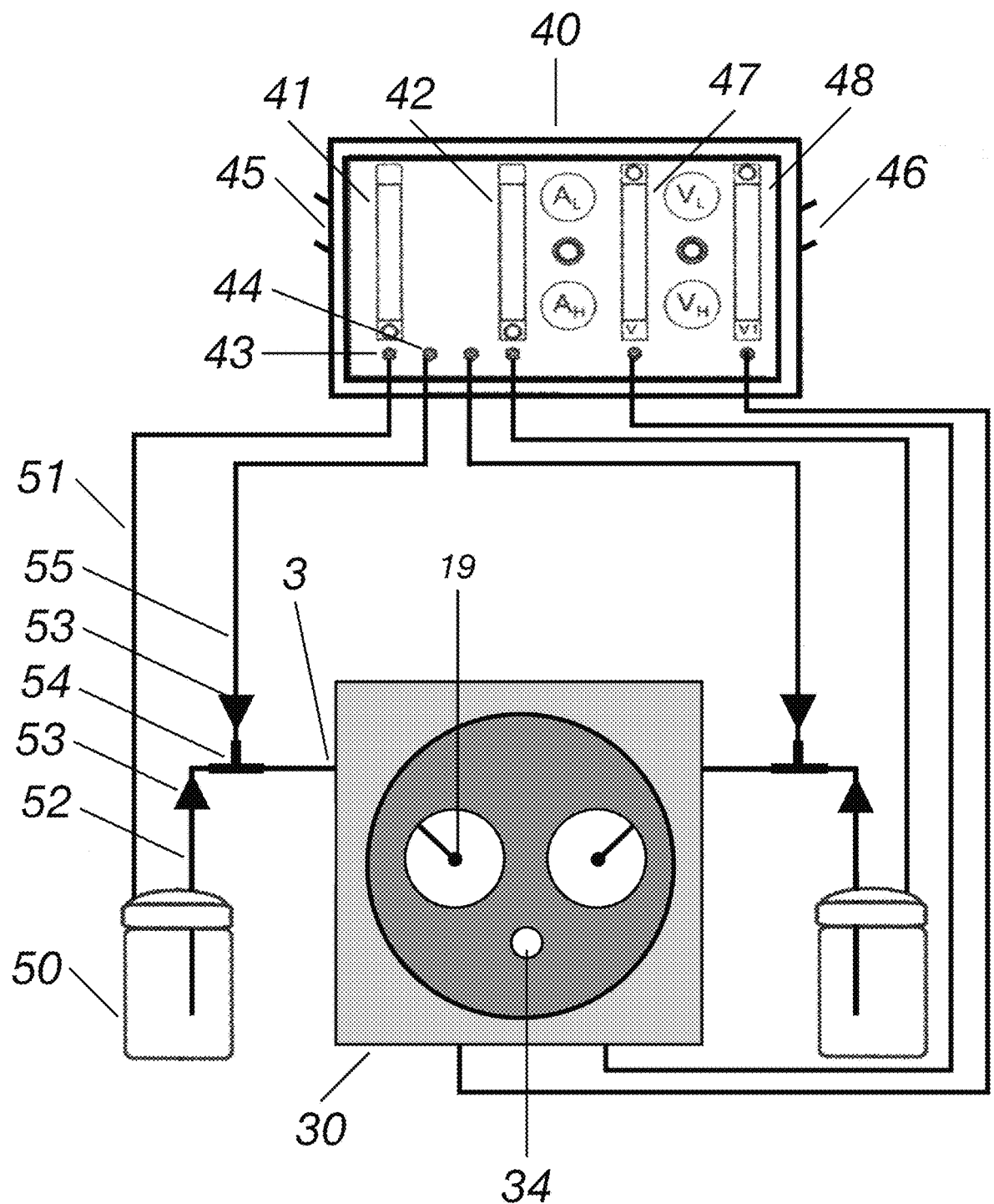
FIG. 10 is a schematic of an olfactometer of the present invention similar to FIG. 9 but embodying the coaxial (fountain) design. [Complete assembly of coaxial olfactometry system.]

FIG. 10 is a schematic of the complete assembly of the olfactometer in the coaxial (fountain) mode. All components are the same as FIG. 9 except for 19 (the inlet tube) whereby the inlet is in the coaxial (fountain) mode.

EXAMPLES

Example 1. (Construction of an Olfactometer)

The basic design of various embodiments of an olfactometer of the present invention is shown in FIGS. 1, 2, 3, 4, 5, 6, and 7. FIGS. 1, 2, 3, 4, and 5 show how glass traps 10 are inserted onto the O-ringed stubs 8. The arena base plate 1 is aligned over the aligning studs 31 (FIG. 6). Next the glass dome 7 is placed on top of the base plate 1 and the chamber aligning plate 32 is mounted over the glass dome 7 and aligned with the aligning studs 31 and secured via the knobs 33. FIG. 6 shows a 4 port base plate made out of a 12"×12"×⅜" 50 series aluminum with four equally spaced 30 mm holes 80 mm from the center and one threaded 1" hole at the center. The stand is constructed from 1" 1004 Profile 80/20 aluminum. The chamber aligning plate (32) is ¼'"×12"×12" acrylic plate with a centered 9.03" diameter hole and four ⁵⁄₁₆" aligning holes.

FIG. 4 shows the glass trap with the inlet tube 19 and impinging cap 35, and vacuum outlet side arm 11; Referring to FIG. 4, a 011 Viton O-ring 9 is affixed to the glass inlet tube 19 which is inserted into the cap 13. This inlet tube/cap assembly is positioned into the bottom inlet arm of the trap 10 and the cap 13 is tightened after the inlet tube is adjusted to the desired height (0 to 180 mm) above the arena base plate 1. Finally, the impinging caps 35 are affixed to the top of the inlet tubes. FIG. 1 shows the glass test chamber 7 and the subject introduction tube 25. The chamber 7 is placed onto the arena base plate 1 with the aligning plate 32 [see FIG. 6]. After the specimens are contained in the introduction tube 25, the tube is inserted into the top #35 GL fitting 15 on the chamber 7 and lowered to the desired height. Insects are released by lowering the rod 26(see FIG. 8). Referring to FIGS. 9 and 10, the clean air is adjusted to the desired flow from the air delivery system 40 and introduced to the connecting inlet tubes 55, 51). Teflon tubing (¼") connects the outlet port 11 on each glass trap 10 [see FIG. 3] to the vacuum inlet on the air delivery system 46 [FIGS. 9 and 10] and exiting air is adjusted to exceed the inlet air flow by 2-5%. This condition establishes an odor-free steady-state environment for acclimation. After an appropriate acclimation period, the specimens are slowly pushed out of the introduction tube 25 for release into the odor-free enclosure 21 [see FIG. 1]. Then the experiment is begun by introducing the test compounds to the test chamber from the external odor source chamber 50 via the diverter switch 45 [FIGS. 9 and 10] and the response observed. FIGS. 9 and 10 show the two ¼" Teflon tubing connections to the diverter switch 45 on the clean air source system 40. One Teflon tube goes to the inlet #7 thread of the external odor source chamber 50 and the other to one arm of the bypass tee 54. Teflon tubing outlet connector 3 connects element 54 to element 19. The glass traps 10 are of 75-mm OD×2.5 mm wall Simax®, 70-mm OAL with 6-mm thick 90-mm OD surface ground flat flanges on top and two #7 ChemThread joints (see FIGS. 1 and 7). The glass inlet tubes 19 are ¼" OD Medium wall Simax® 9" in length with a slotted exit top. Twelve-mm×27-mm bell-shaped Simax® glass impingement caps 35 are seated onto the top end of the inlet tubes 19. This provides the conditions for a discrete odor zone as seen in FIGS. 1, 4 and 5.

Each gas outlet 2 is a 30-mm hole in the arena base plate 1. Each outlet hole has its own isolated (individual) glass trap 10. The chamber of the olfactometer 7 is a dome-shaped Simax® glass cylinder 10" OAL of 5- to 6-mm wall ground flat at the bottom to make an airtight seal on the base plate 1 and a #35 GL thread on the top 15.

FIGS. 9 and 10 depict two typical external odor source chambers 50. Note that these chambers may be any of several designs. A 25-mm diameter port is located in the center top of the chamber 7, which can accept a 24.9-mm OD glass insect retaining tube 26 for introducing insect test subjects into the enclosed space 21. The delivery tube can be raised and lowered and is equipped with a screen 27, and a porous plug 28 allowing inert gas flow into the enclosed space. Each outlet hole 2 is connected to a trap 10 for collecting insects that choose a specific discrete odor zone (3 or 4) and the vapors are exited through a vacuum outlet port 11 on the trap 10 with a tube connected to a vacuum source.

Example 2. (Use of an Olfactometer to Observe Insect Behavior)

Most olfactory choice tests for average size flying insects rely on wind tunnels. This example describes how the olfactometer can test responses of flying insects and corroborate the results with the wind tunnel results.

An olfactometer as described before was scrupulously cleaned. All glass and metal parts i.e., glass traps, glass chamber, base plate, sample introduction tube, caps and inlet tubes were cleaned with 70% isopropanol and placed in an oven at 300° C. for 2 hours and allowed to cool to room temperature. Twenty-five host-seeking, female *Ae. Albopictus* were placed into the introduction tube. The pressure on the inlet of the air delivery system was 110 psi and regulated to 35 psi. The vacuum on the air system was at 18 inches Hg. Inlet flowmeter #1 had the diverter ports for bypass and external odor source #1 connected and adjusted to 1 liter/min. Inlet flowmeter #2 had the diverter ports for bypass and external odor source #2 connected and also set to deliver 1 liter/min. Inlet flowmeters #3 and #4 were set to deliver just clean air, also at 1 liter/minute. All outlet flowmeters (1-4) were set to 1.1 liters/minute. The olfactometer and external odor source chambers were maintained at 26±1° C. with a Relative Humidity of 65%±5%. After a steady state of air flow to all four odor zones, the specimen introduction tube was inserted into the test chamber and allowed to acclimate for 10 minutes; then the mosquitos were released into the enclosed space. After two minutes, the diverter switches on inlets #1 and #2 were positioned to allow the test samples into the odor zones #1 and #2 of the test chamber. The mosquitoes were exposed to these conditions for 20 minutes with a video recording the results. Then the diverter switch was repositioned to the clean state and $CO_2$ was introduced for knockdown. After all subjects in the chamber were immobilized, the olfactometer was opened for vacuum removal of the mosquitoes on the base plate and counting of those mosquitoes in the traps. External odor chamber #1 had Onslaught Fast Cap. External odor chamber #2 contained skin lure (BG-Lure cartridge, BioGentsnAG, Regensberg, Germany).

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

Having generally described this invention, those skilled in the art will appreciate that the present invention contemplates the embodiments of this invention as defined in the following claims, and equivalents thereof. However, those skilled in the art will appreciate that the scope of this invention should be measured by the claims appended hereto, and not merely by the specific embodiments exemplified herein. Those skilled in the art will also appreciate that more sophisticated technological advances will likely appear subsequent to the filing of this document with the patent office. To the extent that these later developed improvements embody the operative principles at the heart of the present disclosure, those improvements are likewise considered to come within the ambit of the following claims. In light of the general disclosure provided hereinabove, with respect to the manner of practicing this inventive method, those skilled in the art will appreciate that this disclosure enables the practice of the inventive method according to the aspects and embodiments disclosed above. The details provided ensure a complete written description of this invention, including the best mode thereof. However, it will be appreciated that the scope of this invention should not be construed in terms of the specific examples provided. It is to be understood that the present invention may have various other embodiments. Furthermore, while the form of the invention herein shown and described constitutes exemplary embodiment of the invention, it is not intended to illustrate all possible forms thereof. It will also be understood that the words used are words of description rather than limitation, and that various changes may be made without departing from the spirit and scope of the invention disclosed. The scope of the invention should not be limited solely to the examples given.

The invention claimed is:

1. An olfactometer comprising:
   a) an enclosure comprising a floor, wall and lid, which together define an enclosed space containing gaseous fluid,
   b) means for generating two or more discrete odor zones within said enclosed space, said means for generating comprising an inlet to deliver a gaseous fluid and an outlet to remove said gaseous fluid for each of the discrete odor zones to be generated by said means, wherein said inlet and outlet are positioned so that each discrete odor zone is will be spatially separated from every other discrete odor zone within said enclosed space by at least a portion of a background odor zone within said enclosed space, and size, shape, position, uniformity, and intensity of each of the discrete odor zones are established by size, position, and geometry of the inlet and outlet, and composition and rate of gaseous fluid flow,
   c) means for controlling the composition and rate of gas flow through the inlet and outlet for each of the discrete odor zones,
   d) means for inserting and releasing at least one live organism test subject into said enclosed space, and
   e) means for permitting detection of a sensory response to one or more of the discrete odor zones by said at least one live organism, and
   wherein at least one of said inlets for delivering gaseous fluid comprises an inner pipe, and at least one of said outlets to remove said gaseous fluid comprises an outer pipe having a greater diameter than the inner pipe, and wherein the inner pipe extends within and protrudes through the outer pipe.

2. The olfactometer of claim 1, wherein said lid and wall together comprise a transparent dome, and the means for permitting detection of a sensory response is to a transparent dome through which can be viewed behavior by the live organism test subject that occurs when the live organism test subject is in a selected discrete odor zone.

3. The olfactometer of claim 1, wherein the inlets and outlets for each of the discrete odor zones comprise holes, ports, tubes, or pipes.

4. The olfactometer of claim 1, wherein said means for controlling the composition and rate of flow of gaseous fluid through the inlets and outlets comprises a diverter that controls the flow of a stream of pressurized gaseous fluid, allowing the composition of the stream to be changed without disrupting the flow rate of the stream.

5. The olfactometer of claim 1 having from two to eight discrete odor-zones distributed within a defined background odor zone in the enclosed space.

6. The olfactometer of claim 1 wherein interior surfaces of the enclosure are of metal, glass, or ceramic.

7. The olfactometer of claim 1, wherein the outlet for a discrete odor zone comprises a hole in the floor of the enclosed space large enough for a live organism test subject to enter, and wherein the olfactometer further comprises a trap downstream from the outlet, said trap comprising means for permitting said live organism test subjects to enter said trap and thereafter be inhibited from re-entering the enclosed space.

8. The olfactometer of claim 1 wherein the floor of the enclosed space has a rough surface to provide traction and facilitate the mobility of walking or crawling organisms.

9. The olfactometer of claim 1 wherein the floor of the enclosed space comprises a removable insert constructed of an inert metal, cellulose, fiberglass, or paper.

10. The olfactometer of claim 1, where the means for inserting and releasing live organism test subjects comprises an inlet for supplemental gas or vapor to enter the enclosed chamber.

11. The olfactometer of claim 1 wherein the enclosure of the olfactometer has a base footprint between 100 and 1,000 $cm^2$, and a height between 10 and 50 cm.

12. A method for applying olfactory response of a live organism test subject to a particular odorant, comprising the steps of:
   a) providing an enclosed space with two or more individual discrete odor zones distributed within or around a defined background odor zone within the enclosed space, comprising an inlet to deliver a gaseous fluid and an outlet to remove said gaseous fluid for each of the discrete odor zones to be generated by said means, wherein at least one of said inlets for delivering gaseous fluid comprises an inner pipe, and at least one of said outlets to remove said gaseous fluid comprises an outer pipe having a greater diameter than the inner pipe, and wherein the inner pipe extends within and protrudes through the outer pipe,
   b) introducing a live arthropod test subject into the defined background odor zone,
   c) recording whether the live arthropod test subject is attracted or repelled to the odorant present in each discrete odor zone, and
   d) if the particular odorant is found to be an attractant for the arthropod, deploying the odorant in pertinent concentration to attract such organisms to places where they are not undesirable, and
   e) if the particular odorant is found to be a repellant, deploying the odorant in pertinent concentration to repel such organisms away from places where they are undesirable.

13. The method of claim 12 wherein the enclosed space contains from 2 to 8 individual discrete odor test zones distributed within or around a defined background odor zone within the enclosed space.

14. A method for applying olfactory response of a live organism test subject to a particular odorant, comprising the steps of:
   a. providing an enclosed space with two or more individual discrete odor zones distributed within or around a defined background odor zone within the enclosed space,
   b. causing the organism test subject to enter a background odor zone within the enclosure,
   c. generating two or more discrete odor zones within said enclosed space, by means comprising an inlet to deliver a gaseous fluid and an outlet to remove said gaseous fluid, for each of the discrete odor zones, wherein said inlet and outlet for each discrete odor zone is positioned so that each discrete odor zone is spatially separated from every other discrete odor zone within said enclosed space by at least a portion of a background odor zone within the space, wherein at least one of said inlets for delivering gaseous fluid comprises an inner pipe, and at least one of said outlets to remove said gaseous fluid comprises an outer pipe having a greater diameter than the inner pipe, and wherein the inner pipe extends within and protrudes through the outer pipe, d. introducing a live arthropod test subject into the defined background odor zone, e. recording the behavior of the live arthropod test subject in response to the odorant, and f. if the particular odorant is found to be an attractant for the arthropod, deploying the odorant in pertinent concentration to attract such organisms to places where they are not undesirable, and g. if the particular odorant is found to be a repellant, deploying the odorant in pertinent concentration to repel such organisms away from places where they are undesirable.

15. A method for operating an olfactometer comprising the steps of:

a) inserting and releasing an organism test subject into an olfactometer enclosure comprising a floor, wall and lid, which together define an enclosed space containing gaseous fluid, b) causing the organism test subject to enter a background odor zone within the enclosure, c) generating two or more discrete odor zones within said enclosed space, by means comprising an inlet to deliver a gaseous fluid and an outlet to remove said gaseous fluid, for each of the discrete odor zones, wherein said inlet and outlet for each discrete odor zone is positioned so that each discrete odor zone is spatially separated from every other discrete odor zone within said enclosed space by at least a portion of a background odor zone within the space, wherein at least one of said inlets for delivering gaseous fluid comprises an inner pipe, and at least one of said outlets to remove said gaseous fluid comprises an outer pipe having a greater diameter than the inner pipe, and wherein the inner pipe extends within and protrudes through the outer pipe, d) controlling gas flow through the inlet and outlet port for each of the one or more discrete odor zones, including composition and rate of gas flow, so that at least one of said discrete odor zones contains a gaseous fluid comprising a composition believed to be detectable as an odorant, and e) observing and recording behavior indicative of sensory response by the organism test subject to one or more of the discrete odor zones.

16. The method of claim 15 wherein the organism test subject is an arthropod.

17. An olfactometer comprising:

a) an enclosure comprising a floor, wall, and lid, which together define an enclosed space containing gaseous fluid, b) one or more defined background odor zones within said enclosed space, c) two or more discrete odor zones within said enclosed space, wherein each discrete odor zone is surrounded by said background odor zone and is spatially separated from and does not overlap or intersect with another discrete odor zone within said enclosed space, d) one or more inlets for delivering gaseous fluid, and one or more outlets for removing gaseous fluid, wherein at least one of said inlets for delivering gaseous fluid comprises an inner pipe, and at least one of said outlets to remove said gaseous fluid comprises an outer pipe having a greater diameter than the inner pipe, and wherein the inner pipe extends within and protrudes through the outer pipe; a means for controlling composition of gaseous fluid; a means of controlling pressure and rate of flow of gaseous fluid through the inlets and outlets, e) a means for inserting and releasing at least one live organism test subject into said enclosed space, and f) a means for detecting a sensory response to one or more of the discrete odor zones by said at least one live organism, wherein the size, shape, position, uniformity, and intensity of the discrete odor zones and defined background zones are established by size, position, and geometry of the inlets and outlets, and by controlling the composition, pressure, and rate of flow of gaseous fluid through the inlets and outlets.

* * * * *